United States Patent
Furukawa et al.

[11] Patent Number: 6,080,895
[45] Date of Patent: Jun. 27, 2000

[54] PROCESS OF PRODUCING CATECHOL DERIVATIVES

[75] Inventors: Yoshiro Furukawa, Osaka; Keishi Takenaka, Amagasaki, both of Japan

[73] Assignee: Daiso Co., Ltd., Osaka, Japan

[21] Appl. No.: 09/091,525

[22] PCT Filed: Dec. 13, 1996

[86] PCT No.: PCT/JP96/03650

§ 371 Date: Jun. 19, 1998

§ 102(e) Date: Jun. 19, 1998

[87] PCT Pub. No.: WO97/22574

PCT Pub. Date: Jun. 26, 1997

[30] Foreign Application Priority Data

Dec. 19, 1995  [JP]  Japan ................................... 7-330315

[51] Int. Cl.[7] .................................................. C07C 37/60
[52] U.S. Cl. ......................... 568/803; 568/749; 568/771; 568/800
[58] Field of Search ..................... 568/716, 731, 568/732, 734, 749, 755, 762, 771, 774, 800, 803, 426, 437, 438, 441

[56] References Cited

U.S. PATENT DOCUMENTS 4,151,201   4/1979   Casnati et al. ....................... 260/562 A

FOREIGN PATENT DOCUMENTS

| | | |
|---|---|---|
| 34737 | of 1978 | Japan . |
| 58-72536 | 4/1983 | Japan . |
| 166637 | of 1985 | Japan . |
| 1-83042 | 3/1989 | Japan . |
| 305546 | 10/1992 | Japan . |
| 5-112485 | 5/1993 | Japan . |

OTHER PUBLICATIONS

Greene, Protective Groups in Organic Synthesis, p. 93, 1981.
J. Org. Chem. 1984, 49, pp. 4740–4741.
Journal of Molecular Catalysis, 14 (1982), pp. 333–340.
Bull. Chem. Soc. Jpn., 62, pp. 1652–1657 (1989).
Chemistry Letters, pp. 179–180, 1972.
J. Chem Soc., Perkin Trans I, pp. 1862–1865 (1980).
J. Chem. Soc., Perkin Trans I, pp. 1353–1354 (1974).
Indian Journal of Chemistry vol. 23B, May, 1984, pp. 474–475.
J Chem. Soc., Perkin Trans I, pp. 1823–1831 (1994).
Nippon Kagaku Kaishi 1979, (3), pp. 370–374.

Primary Examiner—Gary Geist
Assistant Examiner—Sreeni Padmanabhan
Attorney, Agent, or Firm—Jacobson, Price, Holman & Stern PLLC

[57] ABSTRACT

An improved process for producing a catechol derivative (1) useful as a intermediate of pharmaceuticals and agricultural chemicals, being shown by the following reaction scheme. The process is characterized in that formulation in the first step is carried out in the two stages, that is, the reaction is carried out in the presence of a tin catalyst at 60–85° C. to a conversion of 30 to 80% and then is completed at 95–105° C. to produce a salicylaldehyde derivative (3) in a high yield and a high selectivity. Thereby, the objective catechol derivative (1) can be obtained in a high yield and with a high purity.

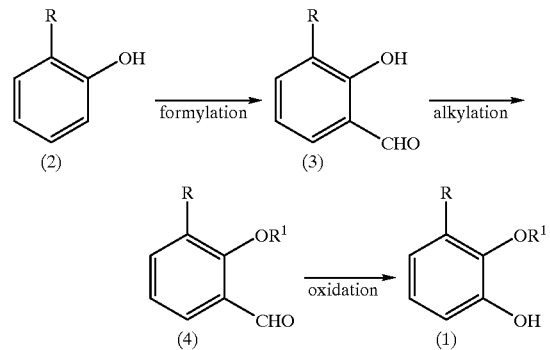

In the above formula, R is alkyl, cycloalkyl, aralkyl, alkoxy, halogen atom, allyl, or aryl, and $R^1$ is a hydroxy protective group.

9 Claims, No Drawings

PROCESS OF PRODUCING CATECHOL DERIVATIVES

This is the U.S. National Stage Application of PCT/JP96/03650 filed Dec. 13, 1996 now WO 97/22574 published Jun. 26, 1997.

TECHNICAL FIELD

This invention relates to an improved process for preparing a catechol derivative represented by a generic formula (1) mentioned later, which constitutes a basic structure of a compound useful especially for pharmaceuticals and agricultural chemicals and is used as an intermediate thereof.

BACKGROUND ART

Monoalkylcatechol derivatives are used as intermediates for pharmaceuticals and agricultural chemicals. The method of preparing them by alkyl-etherification of only a hydroxy group on one side of a corresponding catechol derivative and the method of preparing them by hydroxylation of a corresponding alkoxybenzene derivative have been mainly known. As to the former, the alkyl-ether method by dialkyl sulfate (Japanese Patent Publication (A) No. 112485/1993), and the alkyl-ether method by an alcohol and an acid catalyst (Japanese Patent Publication (A) No. 305546/1992) are illustrated. As to the latter, the method by reaction with hydrogen peroxide under formic acid (Bull. Chem. Soc. Jpn., 1989, 62, 1652–1657), the method by reaction with Fe (IV)-EDTA ascorbic acids (J. Mol. Catal. 1982, 14, 333–340), the method by reaction with peracetic acid (Nippon Kagaku Kaishi 1979, 370–374), and the method of synthesis by photo oxidization under Lewis acid (Chem. Lett., 1972, 179–180) are illustrated.

However, the above known methods are generally inferior in a yield and a position-selectivity. Accordingly, the mixture of regioisomers forms and it is difficult to separate each other so that these methods are not suitable for preparing the intermediates of pharmaceuticals and agricultural chemicals which require high purity. Expensive reagents and raw materials which are difficult to obtain, are sometimes used and therefore, these known methods are not satisfied in the industrial production.

The present inventors engaged extensively in solving the above problems, and have found a new process for preparation of a catechol derivative almost without any by-products and in a high yield and that in a high purity almost without contamination of regioisomers.

DISCLOSURE OF INVENTION

The present invention provides to a process for preparing a catechol derivative represented by the following generic formula (1),

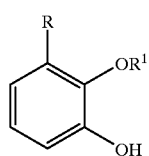

(1)

and is characterized in preparing the catechol derivative by the following three steps:

(I) a step for preparing a salicylaldehyde derivative represented by the following generic formula (3),

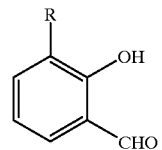

(3)

by reacting a phenol derivative represented by the following formula (2),

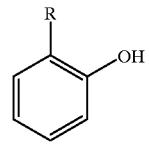

(2)

with a base and paraformaldehyde in the presence of $SnCl_2$ and/or $SnCl_4$ in an organic solvent at 60–85° C. until attaining the conversion to 30–80% and then completing the reaction at 95–105° C.;

(II) a step for preparing a formyl ether represented by the following generic formula (4),

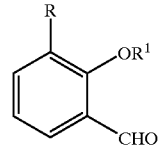

(4)

by treating a salicylaldehyde derivative of the formula (3) by an alkylating agent in the presence of a base in water and/or an organic solvent to introduce a hydroxy protective group; and (III) a step for preparing a catechol derivative represented by the formula (1) by oxidizing a formyl ether of the formula (4) in water and/or an organic solvent, and then hydrolyzing the product in the presence of an acid or a base.

In the above formulae (1)–(4), R is alkyl, cycloalkyl, aralkyl, alkoxy, halogen atom, allyl, or aryl, $R^1$ is a hydroxy protective group, which is selected from known hydroxy protective groups, and said protective group is preferable one which is not eliminated by oxidation and hydrolysis in the course of the reaction of the step (III). Examples of said protective group are alkyl, benzyl, o-nitrobenzyl, p-methoxybenzyl, and allyl.

The above each step is explained in detail.

In the step (I), as the alkyl in R of a phenol derivative of the formula (2), alkyls blanched or not blanched having 1–4 carbon atoms, such as methyl, ethyl, n-propyl, i-propyl, n-butyl, sec-butyl, tert-butyl, etc.; as the cycloalkyl in the R, cycloalkyls having 3–6 carbon atoms, such as cyclopropyl, cyclobutyl, cyclopentyl, cyclohexyl, etc.; as the aralkyl in the R, phenylalkyls having 1–3 carbon atoms in its alkyl portion, such as benzyl, phenethyl, etc.; as the alkoxy in the R, alkyloxys having 1–4 carbon atoms in its branched or not branched alkyl portion, such as methyloxy, ethyloxy, n-propyloxy, i-propyloxy, n-butyloxy, sec-butyloxy, tert-butyloxy, etc.; as the halogen atom in the R, chlorine atom, bromine atom, iodine atom, etc.; as the aryl in the R, phenyl, o-tolyl, m-tolyl, p-tolyl, etc., are preferably illustrated respectively.

The typical examples of the above phenol derivative are o-cresol, 2-ethylphenol, 2-cyclopropylphenol, 2-cyclobutylphenol, 2-benzylphenol, 2-(phenylethyl) phenol, 2-methyloxyphenol(guaiacol), 2-ethyloxyphenol, 2-chlorophenol, 2-bromophenol, 2-iodophenol, 2-allylphenol, 2-hydroxybiphenyl, 2-(o-tolyl)phenol, etc.

As the bases used in the step (I), there are preferably illustrated aliphatic trialkylamines having 1–10 carbon atoms in their each alkyl portion, such as trimethylamine, triethylamine, tripropylamine, tributylamine, tripentylamine, trihexylamine, triheptylamine, trioctylamine, etc., aromatic amines, such as N,N-dimethylaniline, N,N-diethylaniline, etc., and heterocyclic compounds containing N atom, such as 2,6-lutidine, pyridine, etc.

The reaction in the step (I) is carried out by reacting a phenol derivative, a base and paraformaldehyde in the presence of $SnCl_2$ and/or $SnCl_4$ in an organic solvent at 0–85° C. to the conversion of 30–80%, preferably 50–80% and then to complete the reaction at 95–105° C. to give a salicylaldehyde derivative of the formula (3) in a high yield and in a high selectivity.

In regard to the technique converting a phenol derivative into a salicylaldehyde derivative in the above step (I), the process for preparing a salicylaldehyde derivative by using the same raw material and the same catalyst as in the step (I) at 90–150° C., preferably 110° C. by one stage is known (Japanese Patent Publication (A) No. 34737/1978). However, on the known process, paraformaldehyde used for a raw material causes drastically the thermal degradation or the polymerization reaction preferentially occurs to produce an oligomer as a by-product and therefore, the yield significantly decreases and the position on which an aldehyde group is introduced varies among o-, m-, and p-positions and the position-selectivity is not enough satisfied.

This invention is based on the finding that the production of an undesirable oligomer as a by-product is controlled and an aldehyde group is introduced only on the o-position and as a result, an objective salicylaldehyde derivative can be obtained in a high yield and a high selectivity, by adopting the method that the aldehyde introducing-reaction in the step (I) is carried out by two stages under the specific conditions, and by using this intermediate, the finally objective catechol derivative of the formula (I) can be obtained with a high purity.

In case that the conversion in the first stage is less than 30%, paraformaldehyde, a raw material causes the thermal degradation and a resulting salicylaldehyde derivative is polymerized with paraformaldehyde to decrease significantly the yield in the second stage. In case that the conversion is more than 80%, it takes too many hours in the reaction of the first stage and a resulting salicylaldehyde derivative is polymerized with paraformaldehyde to decrease the yield. Therefore, by controlling the reaction of the first stage within the above mentioned conversion rate at 60–85° C., the reaction is carried efficiently out and a salicylaldehyde derivative is obtained in a high yield.

In the second stage, in case that the reaction temperature is lower than 95° C., it takes too many hours to complete the reaction, and in case that the reaction temperature is higher than 105° C., the yield significantly decreases due to the degradation of paraformaldehyde, a raw material, or the polymerization of a resulting salicylaldehyde derivative.

The amount of $SnCl_2$ and/or $SnCl_4$ used in the step (I) is 0.025–5 mol equivalents to a phenol derivative, a starting material, preferably 0.025–1 mol equivalent, and the amount of a base is 0.1–20 mol equivalents to said phenol derivative, preferably 0.1–4 mol equivalents. The amount of paraformaldehyde is 2–10 mol equivalent to said phenol derivative, preferably 2–5 mol equivalents.

The organic solvents used are aromatic solvents, such as benzene, toluene, xylene, etc., ethers, such as diethyl ether, tetrahydrofuran, 1,4-dioxane, 1,2-dimethoxyethane, diglyme, triglyme, diethylene glycol monomethyl ether, etc., chlorinated solvents, such as dichloromethane, dichloroethane, chloroform, etc., and a mixture thereof may be also used.

A salicylaldehyde derivative thus obtained may be isolated and purified by distillation etc., but the product without purification may be used as a starting material in the next step (II).

The reaction in the step (II) is in obtaining the formyl ether of the formula (4), which is the hydroxy protected product, by reacting a salicylaldehyde derivative prepared according to the above step (I) with an alkylating agent in the presence of a base in water and/or an organic solvent by the usual manner in order to obtain said compound. As the alkylating agents, halogenated compounds, such as alkyl halide, aralkyl halide, allyl halide, etc., and dialkyl sulfate are illustrated.

As the alkyl halides, there are exemplified alkyl halides having 1–4 carbon atoms, such as methyl chloride, methyl bromide, methyl iodide, ethyl chloride, ethyl bromide, ethyl iodide, propyl chloride, propyl bromide, propyl iodide, butyl chloride, butyl bromide, butyl iodide, etc.

As the aralkyl halides, there are exemplified phenylalkyl halides in which the benzene ring may be substituted by halogen atom, nitro, alkoxy having 1–4 carbon atoms, or alkyl having 1–4 carbon atoms and in which the alkyl portion has 1–4 carbon atoms, such as benzyl chloride, benzyl bromide, benzyl iodide, o-nitrobenzyl chloride, o-nitrobenzyl bromide, o-nitrobenzyl iodide, p-methoxybenzyl chloride, p-methoxybenzyl bromide, p-methoxybenzyl iodide, etc.

As the allyl halides, there are illustrated allyl chloride, allyl bromide, etc. As the dialkyl sulfates, there are illustrated dialkyl sulfates in which each alkyl has 1–4 carbon atoms, such as dimethyl sulfate, diethyl sulfate, etc.

The amount of the alkylating agent is 1–5 mol equivalents to a salicylaldehyde derivative, preferably 1–3 mol equivalents.

As the bases used in the step (II), there are preferably illustrated alkali metal or alkaline earth metal hydrides, oxides, hydroxides, carbonates, or hydrogen carbonates, such as inorganic bases, such as potassium hydride, sodium hydride, calcium hydride, potassium oxide, sodium oxide, calcium oxide, potassium hydroxide, sodium hydroxide, potassium carbonate, sodium carbonate, calcium carbonate, potassium hydrogencarbonate, sodium hydrogencarbonate, calcium hydrogencarbonate, organic bases, such as alkoxides (e.g. potassium methoxide, potassium ethoxide, sodium methoxide, sodium ethoxide, etc.), and alkyllithiums (e.g. methyllithium, ethyllithium, n-butyllithium, sec-butyllithium, tert-butyllithium, phenyllithium, etc.)

The amount of the above base is 1–5 mol equivalents to a salicylaldehyde derivative, preferably 1–3 mol equivalents.

The solvents used in step (II) are aromatic solvents, such as benzene, toluene, xylene, etc., ethers, such as diethyl ether, tetrahydrofuran, 1,4-dioxane, 1,2-dimethoxyethane, diglyme, triglyme, diethylene glycol monomethyl ether, etc., chlorinated solvents, such as dichloromethane, dichloroethane, chloroform, etc., aprotic solvents, such as N,N-dimethylformamide, dimethyl sulfoxide, sulfolane, hexamethylphosphoramide, etc., ketones, such as acetone, methyl ethyl ketone, methyl iso-propyl ketone, etc., alcohols, such as methanol, ethanol, i-propanol, etc., acetonitrile, water, and so on. A mixture thereof may be used.

The reaction temperature in the step (II) is preferably from 20° C. to the boiling point of the solvent. In case that the reaction temperature is too low, the reaction rate decreases significantly and the yield decreases. Therefore, the low temperature should be avoided.

The formyl ether thus prepared may be isolated or purified, but the product without purification may be used as a starting material in the next step.

In this invention, in the step (III), the object compound, catechol derivative is obtainable by oxidizing a formyl ether with a oxidizing agent in water and/or an organic solvent, followed by hydrolysis in the presence of a base or an acid, but when the oxidation is carried out in the presence of a base or an acid, the hydrolysis occurs together with the oxidation to obtain the objective compound at once. (J. Org. Chem. 1984, 49, 4740–4741, Japanese Patent Publication (A) No.166637/1985) In this case once a formate of the following formula (5) or its equivalent forms, but the product seems to be changed into a catechol derivative at once.

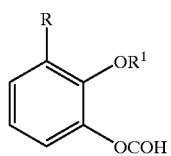

(5)

wherein R and $R^1$ are the same as defined in the formula (1).

The oxidizing agents used in the step (III) are preferably peroxides, as typical ones, such as hydrogen peroxide, m-chloroperbenzoic acid, peracetic acid, perbenzoic acid, monoperoxyorthophthalic acid, monoperoxymaleic acid, peroxyformic acid, p-nitroperbenzoic acid, tert-butylperoxide, etc.

The amount of the oxidizing agent is 1–5 mol equivalents to a formyl ether, preferably 1–3 mol equivalents.

The acids used in the step (III) are mineral acids, such as hydrochloric acid, sulfuric acid, nitric acid, phosphoric acid, etc., acidic salts of a mineral acid, such as sodium hydrogensulfate, potassium hydrogensulfate, sodium dihydrogenphosphate, etc., organic acids, such as formic acid, acetic acid, methanesulfonic acid, p-toluenesulfonic acid, etc. As the bases, there are illustrated the same inorganic bases or organic bases as used in the step (II). The amount of the acid or the base is 0.1–5 mol equivalents to a formyl ether, preferably 0.1–3 mol equivalents.

The solvents used in the step (III) are the same organic solvent as used in the step (I), such as aromatic solvents, ethers, chlorinated solvents and alcohols (e.g. methanol, ethanol, i-propanol, etc.), and water. A mixture thereof may be used.

The reaction temperature on oxidation and hydrolysis in the step (III) is from 0° C. to the boiling point of the solvent used, but the low temperature cause to decrease the reaction rate significantly and therefore, it is not practical.

BEST MODE FOR CARRYING OUT INVENTION

According to this invention, the objective compound is prepared via the above mentioned three steps, but the compound prepared by the each step without isolation or purification is used in the next step reaction and such the process is also included in this invention.

In the following examples, the examples in which the catalyst in the step (I) was changed and the reaction temperatures in the first stage and the second stage were changed were shown, and the comparative example in which the reaction in the first stage was carried out at the lower temperature than at the temperature limited by this invention was shown. And the comparative example in which the reaction was carried out once (without division into 1st and 2nd stages) was also shown.

As the examples in the step (II), the examples in which a base, an alkylating agent and a solvent were respectively changed were shown. As the examples in the step (III), the examples in which oxidation and hydrolysis under the acidic conditions was carried out at once, and in which oxidation and hydrolysis were separately or independently carried out were shown.

In the following examples, the conversion in the step (I) was calculated by the following equation.

Conversion (%)=area of HPLC on a salicylaldehyde derivative/ area of HPLC on a phenol derivative×100

The above each area is the area of liquid chromatogram which was obtained by the following conditions:
Analytical conditions
Column: Daiso Pack SP-120–5-ODS-AP (Daiso Co., Ltd.)
Mobile phase: phosphoric acid-acetonitrile-water= 0.0001:60:40(volume ratio)
Flow rate: 1.0 ml/min.
Detection: absorbance at 210 nm

EXAMPLE

[I] Process for preparation of salicylaldehyde 1-(1)

o-Cresol 20.0 g (185 mmol) was dissolved in toluene 400 ml and thereto was added 2,6-lutidine 18.4 g (171 mmol). $SnCl_4$ 4.8 g (18 mmol) was added to the mixture and the mixture was stirred for 30 min. at 20° C. Thereto was added paraformaldehyde (purity: 95 weight %) 12.9 g (409 mmol) and the mixture was stirred at 80° C. for 5 hours to the conversion of 78%. And the reaction was kept for 10 hours at 100° C. to confirm the disappearance of the raw material, o-cresol. The reaction solution was cooled to room temperature, extracted with water-toluene in a separatory funnel and the organic layer was dried over anhydrous magnesium sulfate and dried in vacuo to give 2-hydroxy-3-methylbenzaldehyde 24.9 g (yield: 99%, selectivity: 99%).

1-(2)

By using $SnCl_2$ 3.5 g (18 mmol) instead of $SnCl_4$ 4.8 g, in the same manner as in the above 1-(1), except for to the conversion of 70%, there was obtained 2-hydroxy-3-methylbenzaldehyde 24.4 g (yield: 97%, selectivity: 98%).

1-(3)

In the same manner as in the above 1-(1), except for at 65° C. for 7 hours and to the conversion of 51% in the first stage and at 95° C. for 13 hours in the second stage, there was obtained 2-hydroxy-3-methylbenzaldehyde 24.4 g (yield: 97%, selectivity: 99%).

Comparative 1-(1)

In the same manner as in the above 1-(1), except for at 40° C. for 7 hours and to the conversion of 25% in the first stage and at 95° C. for 13 hours in the second stage, there was obtained 2-hydroxy-3-methylbenzaldehyde 10.5 g (yield: 42%, selectivity: 75%).

Comparative 1-(2)

In the same manner as in the above 1-(1), except for at 100° C. for 7 hours and to the conversion of 99% in the first stage, there was obtained 2-hydroxy-3-methylbenzaldehyde 12.0 g (yield: 48%, selectivity: 62%)

Comparative 1-(3)

In the same manner as in the above 1-(1), except for at 70° C. for 35 hours and to the conversion of 99% in the first stage, there was obtained 2-hydroxy-3-methylbenzaldehyde 11.7 g (yield: 47%, selectivity: 60%)

[II] Process for preparation of formyl ether 2-(1)

A solution of 2-hydroxy-3-methylbenzaldehyde 20.0 g (147 mmol) prepared by the above 1-(1) in dimethylformamide (DMF) (100 ml) was added to the suspension of sodium hydride 6.5 g (163 mmol) with purity 60% and DMF (40 ml) under ice-cooling. After completion of emission of hydrogen gas, benzyl bromide 25.0 g (147 mmol) was dropped to it in a ice bath. The reaction mixture was stirred for 4 hours at 20° C. After the disappearance of the raw material, water was added to the reaction mixture and it was extracted with methylene chloride. The organic layer was dried over anhydrous magnesium sulfate, the solvent was removed in vacuo and the residue was purified by silica gel chromatography (n-hexane-ethyl acetate) to give 2-benzyloxy-3-methylbenzaldehyde 29.9 g (yield: 91%).

2-(2)

2-Hydroxy-3-methylbenzaldehyde 20.0 g (147 mmol) prepared by the above 1-(1) was dissolved in dimethylformamide (DMF) (100 ml) and to the solution was added potassium carbonate 31.0 g (221 mmol) and thereto was dropped benzyl bromide 25.0 g (147 mmol). The reaction mixture was stirred for 2 hours at 20° C. After disappearance of the raw material, the reaction mixture was filtrated and the solvent was removed in vacuo and the residue was purified in the same manner as in the above 2-(1) to give 2-benzyloxy-3-methylbenzaldehyde 24.2 g (yield: 73%).

2-(3)

In the same manner as in the above 2-(2) except for dissolving in methyl ethyl ketone (MEK) 100 ml instead of DMF 100 ml, there was obtained 2-benzyloxy-3-methylbenzaldehyde 24.9 g (yield: 75%).

2-(4)

In the same manner as in the above 2-(2) except for dissolving in acetonitrile 100 ml instead of DMF 100 ml, there was obtained 2-benzyloxy-3-methylbenzaldehyde 25.4 g (yield: 77%).

2-(5)

In the same manner as in the above 2-(2) except for using benzyl chloride 18.6 g (147 mmol) instead of benzyl bromide 25.9 g, and at 50° C. (reaction temperature), there was obtained 2-benzyloxy-3-methylbenzaldehyde 25.9 g (yield: 79%).

[III] Process for preparation of catechol derivative 3-(1)

2-Benzyloxy-3-methylbenzaldehyde prepared by the above 2-(1) 20.0 g (88.4 mmol) was dissolved in methanol 100 ml and thereto was added sulfuric acid 20.0 g (203 mmol) and then added 30% hydrogen peroxide 30.1 g (265 mmol). The mixture was refluxed for 2 hours. After disappearance of the raw material, the solution was concentrated in vacuo, neutralized with a saturated sodium bicarbonate solution and extracted with methylene chloride. The solvent was removed in vacuo and the residue was purified by silica gel chromatography (n-hexane-ethyl acetate) to give 2-benzyloxy-3-methylphenol 13.3 g (yield: 70%).

3-(2)

2-Benzyloxy-3-methylbenzaldehyde prepared by the above 2-(1) 20.0 g (88.4 mmol) was dissolved in methylene chloride 100 ml and thereto was added m-chloroperbenzoic acid 16.8 g (97.2 mmol). The mixture was reacted at 20° C. under stirring for 10 hours. After disappearance of the raw material, the solution was neutralized with a saturated sodium bicarbonate solution and extracted with methylene chloride. To the extract (2-benzyloxy-3-formyloxytoluene) was added a 10% sodium hydroxide solution 38.9 g (97.2 mmol) in the ice bath and the mixture was stirred for 3 hours. The reaction mixture was neutralized with a 5% hydrochloric acid solution and extracted with methylene chloride. The solvent was removed in vacuo and the residue was purified in the same manner as in the above mentioned 3-(1) to give 2-benzyloxy-3-methylphenol 16.7 g (yield: 88%).

Industrial Applicability

According to this invention, by carrying out the reaction of the step (I) in two stages under the specified conditions, the degradation of paraformaldehyde and the polymerization of paraformaldehyde in the reaction can be controlled and the intermediate without contamination of regioisomers can be obtained in a high yield, and thereby, the finally objective compound, a catechol derivative can be obtained with a high purity.

We claim:

1. A process for preparing a catechol derivative represented by the following generic formula (1),

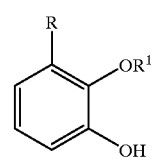

(1)

is characterized in preparing the catechol derivative by the steps consisting essentially of (I) a step for preparing a salicylaldehyde derivative represented by the following generic formula (3),

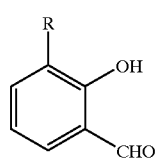

(3)

at a yield of at least 95%, by reacting a phenol derivative represented by the following formula (2),

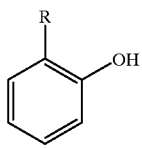

(2)

with a base and paraformaldehyde in the presence of $SnCl_2$ and/or $SnCl_4$ in an organic solvent at 60–85° C. until attaining the conversion to 30–80% and then by completion of the reaction at 95–105° C.;

(II) a step for preparing a formyl ether represented by the following generic formula (4),

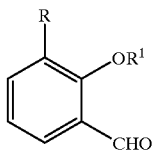

(4)

by treating a salicylaldehyde derivative of the formula (3) by an alkylating agent in the presence of a base in water and/or an organic solvent to introduce a hydroxy protective group; and (III) a step for preparing a catechol derivative of the formula (1) by oxidizing a formyl ether of the formula (4) in water and/or an organic solvent, and then hydrolyzing the product in the presence of an acid or a base, wherein in the above formulae (1)–(4), R is alkyl, cycloalkyl, aralkyl, alkoxy, halogen atom, allyl, or aryl, $R^1$ is a hydroxy protective group.

2. The process for a catechol derivative claimed in claim 1, wherein a base used in the step (I) is a base selected from aliphatic trialkylamines, aromatic amines and heterocyclic compounds containing N atom.

3. The process for a catechol derivative claimed in claim 2, wherein the aliphatic trialkylamine is an amine selected from trialkylamines in which each alkyl portion has 1–10 carbon atoms, the aromatic amine is N,N-dimethylaniline or N,N-diethylaniline, and the heterocyclic compound containing N atom is 2,6-lutidine or pyridine.

4. The process for a catechol derivative claimed in claim 1, wherein the base used in the step (II) is an alkali metal or alkaline earth metal hydride, oxide, hydroxide, carbonate or bicarbonate, or an organic base.

5. The process for a catechol derivative claimed in claim 1, wherein the alkylating agent used in the step (II) is a halogenated compound selected from alkyl halides, aralkyl halides and allyl halides, or a dialkyl sulfate.

6. The process for a catechol derivative claimed in claim 1, wherein the oxidation agent used in the step (III) is a peroxide.

7. The process for a catechol derivative claimed in claim 1, wherein the oxidation agent is an oxidation agent selected from hydrogen peroxide, m-chloroperbenzoic acid, peracetic acid, perbenzoic acid, monoperoxyorthophthalic acid, monoperoxymaleic acid, peroxyformic acid, p-nitroperbenzoic acid, and tert-butylperoxide.

8. The process for a catechol derivative claimed in claim 1, wherein the acid used in the step (III) is a mineral acid selected from hydrochloric acid, sulfuric acid and nitric acid, or an organic acid selected from formic acid, acetic acid, methanesulfonic acid and p-toluenesulfonic acid.

9. The process for a catechol derivative claimed in claim 1, wherein the base used in the step (III) is an alkali metal or alkaline earth metal hydride, oxide, hydroxide, carbonate or bicarbonate, or an organic base.

* * * * *